United States Patent
Deckert et al.

(10) Patent No.: US 9,314,522 B2
(45) Date of Patent: Apr. 19, 2016

(54) ANTITUMORS COMBINATIONS CONTAINING ANTIBODIES RECOGNIZING SPECIFICALLY CD38 AND BORTEZOMIB

(75) Inventors: Jutta Deckert, Waltham, MA (US); Pascale Lejeune, Paris (FR); Michele Mayo, Waltham, MA (US); Peter U. Park, Waltham, MA (US)

(73) Assignee: Sanofi, Paris (FR)

( * ) Notice: Subject to any disclaimer, the term of this patent is extended or adjusted under 35 U.S.C. 154(b) by 15 days.

(21) Appl. No.: 13/992,684

(22) PCT Filed: Dec. 8, 2011

(86) PCT No.: PCT/EP2011/072228
§ 371 (c)(1),
(2), (4) Date: Jan. 2, 2014

(87) PCT Pub. No.: WO2012/076663
PCT Pub. Date: Jun. 14, 2012

(65) Prior Publication Data
US 2014/0186337 A1  Jul. 3, 2014

(30) Foreign Application Priority Data
Dec. 10, 2010 (EP) .................................. 10306395

(51) Int. Cl.
A61K 39/395 (2006.01)
A61K 38/05 (2006.01)
C07K 16/28 (2006.01)

(52) U.S. Cl.
CPC .......... *A61K 39/39558* (2013.01); *A61K 38/05* (2013.01); *A61K 39/3955* (2013.01); *C07K 16/2896* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 3,032,584 | A | 5/1962 | Franz |
| 3,032,585 | A | 5/1962 | Franz |
| 3,116,282 | A | 12/1963 | Hunter et al. |
| 4,281,061 | A * | 7/1981 | Zuk et al. .................... 435/7.9 |
| 4,444,887 | A | 4/1984 | Hoffmann |
| 4,716,111 | A | 12/1987 | Osband et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,639,641 | A | 6/1997 | Pedersen et al. |
| 5,814,318 | A | 9/1998 | Lonberg et al. |
| 7,829,673 | B2 * | 11/2010 | De Weers et al. .......... 530/387.1 |
| 8,153,765 | B2 * | 4/2012 | Park et al. ................... 530/387.3 |
| 8,551,485 | B2 | 10/2013 | Bernett et al. |
| 8,633,301 | B2 * | 1/2014 | Lejeune et al. ............. 530/387.1 |
| 8,877,899 | B2 * | 11/2014 | Rojkjaer et al. ............ 530/387.3 |
| 2008/0057070 | A1 | 3/2008 | Long et al. |
| 2009/0304710 | A1 | 12/2009 | Park et al. |
| 2010/0092489 | A1 * | 4/2010 | Van De Winkel et al. . 424/172.1 |
| 2011/0262454 | A1 | 10/2011 | Park et al. |
| 2011/0274686 | A1 | 11/2011 | Lejeune |
| 2011/0293606 | A1 | 12/2011 | Lejeune |
| 2011/0305690 | A1 | 12/2011 | Lejeune |
| 2012/0161819 | A1 * | 6/2012 | Rossi et al. .................... 327/109 |
| 2014/0161819 | A1 | 6/2014 | Hann et al. |
| 2014/0186337 | A1 | 7/2014 | Deckert et al. |
| 2015/0118251 | A1 | 4/2015 | Deslandes et al. |

FOREIGN PATENT DOCUMENTS

| | | |
|---|---|---|
| CA | 2 333 682 A1 | 8/1999 |
| EP | 0 239 400 A2 | 9/1987 |
| EP | 0 519 596 A1 | 12/1992 |
| EP | 0 592 106 A1 | 4/1994 |
| EP | 1 914 242 A1 | 4/2008 |
| WO | 91/09967 A1 | 7/1991 |
| WO | 91/10741 A1 | 7/1991 |
| WO | 92/22653 A1 | 12/1992 |
| WO | 96/33735 A1 | 10/1996 |
| WO | 96/34096 A1 | 10/1996 |
| WO | 98/16654 A1 | 4/1998 |
| WO | 98/24893 A2 | 6/1998 |
| WO | 98/46645 A2 | 10/1998 |
| WO | 98/50433 A2 | 11/1998 |
| WO | 99/62526 A2 | 12/1999 |
| WO | 00/40265 A1 | 7/2000 |
| WO | 2004026337 A1 | 4/2004 |
| WO | 2005/103083 A2 | 11/2005 |
| WO | 2006/099875 A1 | 9/2006 |
| WO | 2008037257 A2 | 4/2008 |
| WO | WO 2008/047242 A2 | 4/2008 |
| WO | 2008/047242 A9 | 2/2009 |
| WO | 2009/032661 A1 | 3/2009 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | 2012/076663 A1 | 6/2012 |

(Continued)

OTHER PUBLICATIONS

Pascalis et al (The Journal of Immunology (2002) 169, 3076-3084).*
Casset et al. (2003) BBRC 307, 198-205.*
Strome et al., The Oncologist, 2007; 12:1084-95.*
Brand et al., Anticancer Res. 2006; 26:463-70.*
Walsby, et al: The Nf-kB Inhibitor LC-1 Has Single Agent Activity in Multiple Myeloma Cells and Synergizes with Bortezomib; Mol Cancer Ther; 2010, vol. 9, pp. 1574-1582.
International Preliminary Report on Patentability (Written Opinion), PCT/EP2011/072228, dated Dec. 6, 2013, 6 pages.

(Continued)

*Primary Examiner* — Sheela J Huff
(74) *Attorney, Agent, or Firm* — Lathrop & Gage LLP; James H. Velema, Esq.

(57) ABSTRACT

Pharmaceutical composition comprising an antibody specifically recognizing CD38 and bortezomib.

14 Claims, No Drawings

(56) References Cited

FOREIGN PATENT DOCUMENTS

| WO | 2014/089416 A1 | 6/2014 |
|---|---|---|
| WO | 2014/159911 A1 | 10/2014 |
| WO | 2015/066450 A1 | 5/2015 |

OTHER PUBLICATIONS

International Search Report for Application No. PCT/EP2011/072228, dated Feb. 10, 2012 (5 pages).
Written Opinion of the International Searching Authority for Application No. PCT/EP2011/072228, dated Jun. 10, 2013 (5 pages).
Rudikoff et al. 'Single amino acid substitution altering antigen-binding specificity.' Proceedings of the National Academy of Sciences. 1982, vol. 79, No. 6, pp. 1979-1983.
Colman, Peter M. 'Effects of amino acid sequence changes on antibody-antigen interactions.' Research in Immunology. 1994, vol. 145, No. 1, pp. 3-36.
Paul, Fundamental Immunology. "Raven Press." New York. 1993, 292-295.
Bendig. Mary M. 'Humanization of rodent monoclonal antibodies by CDR grafting.' Methods—Companion to Methods in Enzymology. 1995, vol. 8, No. 2, pp. 83-93.
Merck Index, 14th Edition, Entry 0002747, 2006.
Thomas, Deborah A. et al, 'Chemoimmunotherapy with Hyper-CVAD plus Rituximab for the Treatment of Adult Burkitt and Burkitt-Type Lymphoma or Acute Lymphoblastic Leukemia'. 2006 Cancer vol. 106 No. 7 pp. 1569-1580.
Boue, F. et al, 'Phase II Trial of CHOP Plus Rituximab in Patients with HIV-Associated Non-Hodgkin's Lymphoma'. 2006 Journal of Clinical Oncology vol. 24 No. 25 pp. 4123-4128.
Veneri, D. et al, 'Remission of Severe Antiphospholipid Syndrome Associated with non-Hodgkins B-cell Lymphoma after Combined Treatment with Rituximab and Chemotherapy'. 2005 Hematol. Journal vol. 90 No. 10 pp. 104-105.
Keating, Michael J. et al, 'Early Results of a Chemoimmunotherapy Regimen of Fludarabine, Cyclophosphamide, and Rituximab As Initial Therapy for Chonic Lymphocytic Leukemia'. 2005 Journal of Clinical Oncology vol. 23 No. 18 pp. 4079-4088.
Stevenson, George T. et al, 'CD38 as a Therapuetic Target'. 2006 Mol Med vol. 12 Nos. 11-12 pp. 345-346.
Deaglio, S. et al, 'CD38 at the Junction Between Prognostic Marker and Therapeutic Target'. 2008 Trends Mol Med vol. 14 No. 5 pp. 210-218.
Brown et al. (1996) "Tolerance of single, but not multiple, amino acid replacements in antibody VH CDR 2: a means of B cell wastage from somatic hypermutation?" J. Immunol. 156(9):3285-3291.
Caldas et al. (2003) "Humanization of the anti-CD18 antibody 6.7: an unexpected effect of a framework residue in binding to antigen," Mol. Immunol. 39(15):941-952.
Chen et al. (1999) "Selection and analysis of an optimized anti-VEGF antibody: crystal structure of an affinity-matured Fab in complex with antigen," J. Mol. Bio. 293:865-881.
Chien et al. (1989) "Significant structural and functional change of an antigen-binding site by a distant amino acid substitution: proposal of a structural mechanism," Proc. Natl. Acad. Sci. USA. 86:5532-5536.
Corbett et al. (1977) "Evaluation of single agents and combinations of chemotherapeutic agents in mouse colon carcinomas," Cancer 40:2660-2680.
Davies et al. (1996) "Affinity improvement of single antibody VH domains: residues in all three hypervariable regions affect antigen binding," Immunotechnology. 2:169-179.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," J. Immunol. 169(6):3076-3084.
Ellis et al. (1995) "Engineered anti-CD38 monoclonal antibodies for immunotherapy of multiple myeloma" J. Immunol. 155(2):925-937.
Flavell et al. (1995) "Therapy of human T-cell acute lymphoblastic leukaemia with a combination of anti-CD7 and anti-CD38-SAPORIN immunotoxins is significantly better than therapy with each individual immunotoxin," Int. J. Cancer. 62 (3):337-344.
Gamier et al. (2002) "Treatment of post-transplant lymphomas with anti-B-cell monoclonal antibodies," Recent Results Cancer Res. 159:113-122.
Giusti et al. (1987) "Somatic diversification of S107 from an antiphosphocholine to an anti-DNA autoantibody is due to a single base change in its heavy chain variable region," Proc. Natl. Acad. Sci. USA. 84(9):2926-2930.
Gussow et al. (1991) "Humanization of monoclonal antibodies," Methods in Enzymology. 203:99-121.
Holm et al. (2007) "Functional mapping and single chain construction of the anti-cytokeratin 8 monoclonal antibody TS1," Mol. Immunol 44(6):1075-1084.
Holt et al. (2003) "Domain antibodies: proteins for therapy," Trends in Biotechnology. 21(11):484-490.
International Search Report with Written Opinion corresponding to International Patent Application No. PCT/IB2009/055389, mailed Apr. 4, 2010.
International Search Report with Written Opinion corresponding to International Patent Application No. PCT/IB2009/055390, mailed Apr. 6, 2010.
International Search Report with Written Opinion corresponding to International Patent Application No. PCT/IB2009/055391, mailed Apr. 6, 2012.
International Search Report with Written Opinion corresponding to International Patent Application No. PCT/IB2009/055392, mailed Apr. 1, 2010.
Jansen et al. (1993) "Effective immunochemotherapy of human t(4;11) leukemia in mice with severe combined immunodeficiency (SCID) using B43 (anti-CD19)-pokeweed antiviral protein immunotoxin plus cyclophosphamide," Leukemia. 7(2):290-297.
Keren et al. (1999) "Myeloma ascites—a favorable outcome with cyclophosphamide therapy," Am. J. Hematol. 60 (2):140-142.
Kussie et al. (1994) "A single engineered amino acid substitution changes antibody fine specificity," The Journal of Immunology. 152:146-152.
Lamminmaki et al. (2001) "Crystal Structure of a Recombinant Anti-estradiol Fab Fragment in Complex with 17-Estradiol," J. Biol. Chem. 276:36687-36694.
Liu et al. (1999) "Fine mapping of the antigen-antibody interaction of scFv215, a recombinant antibody inhibiting RNA polymerase II from *Drosophila melanogaster*," Journal of Molecular Recognition. 12(2):103-111.
MacCallum et al. (1996) "Antibody-antigen Interactions: Contact Analysis and Binding Site Topography," J. Mol. Biol. 262(5):732-745.
Maloney et al. (1999) "Antibody therapy for treatment of multiple myeloma," Semin. Hematol. 36(1 Suppl. 3):30-33.
Mariuzza et al. (1987) "The Structural Basis of Antigen-Antibody Recognition," Annu. Rev. Biophys. Biophys. Chem. 16:139-159.
Maynard et al. (2000) "Antibody engineering." Annual Review of Biomedical Engineering 2:339-376.
Padlan (1991) "A possible procedure for reducing the immunogenicity of antibody variable domains while preserving their ligand-binding properties," Molecular Immunology. 28:489-498.
Padlan et al. (1989) "Structure of an antibody-antigen complex: crystal structure of the HyHEL-10 Fab-lysozyme complex," Proc. Natl. Acad. Sci. USA. 86:5938-5942.
Paul (1993) Fundamental Immunology. 3rd Ed. William E. Paul, M.D.: Ed. p. 242.
Pini et al. (1998) "Design and use of a phage display library. Human antibodies with subnanomolar affinity against a marker of angiogenesis eluted from a two-dimensional gel," Journal of Biological Chemistry. 273(34):21769-21776.
Roguska et al. (1994) "Humanization of murine monoclonal antibodies through variable domain resurfacing," Proc. Natl. Acad. Sci. USA. 91:969-973.
Schabel et al. (1979) "Testing therapeutic hypotheses in mice and man. Observations on the therapeutic activity against advanced solid tumors of mice treated with anticancer drugs that have demonstrated or potential clinical utility for treatment of advanced solid tumors of man," In; Cancer Drug Development Part B: Methods in Cancer Research. Academic Press. New York, New York. vol. 17. pp. 3-51.

(56) References Cited

OTHER PUBLICATIONS

Schildbach et al. (1994) "Contribution of a single heavy chain residue to specificity of an anti-digoxin monoclonal antibody," Protein Science 3(5):737-749.

Schildbach et al. (1993) "Heavy chain position 50 is a determinant of affinity and specificity for the anti-digoxin antibody 26-10," Journal of Biological Chemistry. 268(29):21739-21747.

Shivakuma et al. (Aug. 2006) Highlights from 6th International Congress of Monoclonal Antibodies in Cancer, Aug. 2006.

Stevenson et al. (1991) "Preliminary studies for an immunotherapeutic approach to the treatment of human myeloma using chimeric anti-CD38 antibody," Blood. 77(5):1071-1079.

Studnicka et al. (1994) "Human-engineered monoclonal antibodies retain full specific binding activity by preserving non-CDR complementarity-modulating residues," Protein Engineering. 7:805-814.

Urushizaki (2003) "Recent View of Tumor Dormancy Therapy," Biotherapy. 17(4):331-338.—English Abstract Only.

Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.

Winkler et al (2000) "Changing the Antigen Binding Specificity by Single Point Mutations of an Anti-p24 (HIV-1) Antibody," J. Immunol. 165:4505-4514.

Wu et al. (1999) "Humanization of a murine monoclonal antibody by simultaneous optimization of framework and CDR residues," J. Mol. Biol. 294(1):151-162.

Xiang et al. (2000) "Study of B72.3 combining sites by molecular modeling and site-directed mutagenesis," Protein Engineering. 13(5):339-344.

Angelopoulou et al. (2002) "The splenic form of mantle cell lymphoma," European Journal of Haematology. 68:12-21.

Domingo-Domenech et al. (2002) "CD38 Expression in B-Chronic Lymphocytic Leukemia: Association With Clinical Presentation And Outcome In 155 Patients," Haematologica. 87:1021-1027.

Kang et al. (2006) "Transcriptional regulation of CD38 expression by tumor necrosis factor-alpha in human airway smooth muscle cells: role of NF-B and sensitivity to glucocorticoids," The FASEB Journal. 20:E170-E179.

Keyhani et al. (1999) "Increased CD38 expression is associated with favorable prognosis in adult acute leukemia," Leukemia Research. 24:153-159.

Lin et al. (2004) "Flow Cytometric Immunophenotypic Analysis of 306 Cases of Multiple Myeloma," American Journal of Clinical Pathology. 121:482-488.

Schwonzen et al. (1993) "Immunophenotyping of low-grade B-cell lymphoma in blood and bone marrow: poor correlation between immunophenotype and cytological/histological classification," Brit. J. Haematol. 83:232-239.

* cited by examiner

```
                              SEQUENCE LISTING

<160> NUMBER OF SEQ ID NOS: 81

<210> SEQ ID NO 1
<211> LENGTH: 5
<212> TYPE: PRT
<213> ORGANISM: Mus sp.

<400> SEQUENCE: 1

Ser Tyr Gly Met Asn
1               5

<210> SEQ ID NO 2
<211> LENGTH: 17
<212> TYPE: PRT
<213> ORGANISM: Mus sp.

<400> SEQUENCE: 2

Trp Ile Asn Thr Tyr Thr Gly Glu Pro Thr Tyr Ala Asp Asp Phe Lys
1               5                   10                  15

Gly

<210> SEQ ID NO 3
<211> LENGTH: 5
<212> TYPE: PRT
<213> ORGANISM: Mus sp.

<400> SEQUENCE: 3

Arg Gly Phe Ala Tyr
1               5

<210> SEQ ID NO 4
<211> LENGTH: 15
<212> TYPE: PRT
<213> ORGANISM: Mus sp.

<400> SEQUENCE: 4

Arg Ala Ser Glu Ser Val Glu Ile Tyr Gly Asn Gly Phe Met Asn
1               5                   10                  15

<210> SEQ ID NO 5
<211> LENGTH: 7
<212> TYPE: PRT
<213> ORGANISM: Mus sp.
```

```
<400> SEQUENCE: 5

Arg Ala Ser Asn Leu Glu Ser
1               5

<210> SEQ ID NO 6
<211> LENGTH: 9
<212> TYPE: PRT
<213> ORGANISM: Mus sp.

<400> SEQUENCE: 6

Gln Gln Ile Asn Glu Asp Pro Phe Thr
1               5

<210> SEQ ID NO 7
<211> LENGTH: 5
<212> TYPE: PRT
<213> ORGANISM: Mus sp.

<400> SEQUENCE: 7

Asn Ser Gly Met Asn
1               5

<210> SEQ ID NO 8
<211> LENGTH: 17
<212> TYPE: PRT
<213> ORGANISM: Mus sp.

<400> SEQUENCE: 8

Trp Ile Asn Thr Tyr Thr Gly Glu Pro Thr Tyr Ala Asp Asp Phe Lys
1               5                   10                  15

Gly

<210> SEQ ID NO 9
<211> LENGTH: 5
<212> TYPE: PRT
<213> ORGANISM: Mus sp.

<400> SEQUENCE: 9

Arg Gly Phe Val Tyr
1               5

<210> SEQ ID NO 10
<211> LENGTH: 15
<212> TYPE: PRT
<213> ORGANISM: Mus sp.

<400> SEQUENCE: 10

Arg Ala Ser Glu Ser Val Ala Ile Tyr Gly Asn Ser Phe Leu Lys
1               5                   10                  15

<210> SEQ ID NO 11
<211> LENGTH: 7
<212> TYPE: PRT
<213> ORGANISM: Mus sp.

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Mus sp.
```

<400> SEQUENCE: 12

Gln Gln Ile Asn Glu Asp Pro Tyr Thr
1               5

<210> SEQ ID NO 13
<211> LENGTH: 5
<212> TYPE: PRT
<213> ORGANISM: Mus sp.

<400> SEQUENCE: 13

Asp Tyr Trp Met Gln
1               5

<210> SEQ ID NO 14
<211> LENGTH: 17
<212> TYPE: PRT
<213> ORGANISM: Mus sp.

<400> SEQUENCE: 14

Thr Ile Tyr Pro Gly Asp Gly Asp Thr Gly Tyr Ala Gln Lys Phe Lys
1               5                   10                  15

Gly

<210> SEQ ID NO 15
<211> LENGTH: 11
<212> TYPE: PRT
<213> ORGANISM: Mus sp.

<400> SEQUENCE: 15

Gly Asp Tyr Tyr Gly Ser Asn Ser Leu Asp Tyr
1               5                   10

<210> SEQ ID NO 16
<211> LENGTH: 11
<212> TYPE: PRT
<213> ORGANISM: Mus sp.

<400> SEQUENCE: 16

Lys Ala Ser Gln Asp Val Ser Thr Val Val Ala
1               5                   10

<210> SEQ ID NO 17
<211> LENGTH: 7
<212> TYPE: PRT
<213> ORGANISM: Mus sp.

<400> SEQUENCE: 17

Ser Ala Ser Tyr Arg Tyr Ile
1               5

<210> SEQ ID NO 18
<211> LENGTH: 9
<212> TYPE: PRT
<213> ORGANISM: Mus sp.

<400> SEQUENCE: 18

Gln Gln His Tyr Ser Pro Pro Tyr Thr
1               5

<210> SEQ ID NO 19
<211> LENGTH: 5
<212> TYPE: PRT
<213> ORGANISM: Mus sp.

```
<400> SEQUENCE: 19

Gly Ser Trp Met Asn
1               5

<210> SEQ ID NO 20
<211> LENGTH: 17
<212> TYPE: PRT
<213> ORGANISM: Mus sp.

<400> SEQUENCE: 20

Arg Ile Tyr Pro Gly Asp Gly Asp Ile Ile Tyr Asn Gly Asn Phe Arg
1               5                   10                  15

Asp

<210> SEQ ID NO 21
<211> LENGTH: 10
<212> TYPE: PRT
<213> ORGANISM: Mus sp.

<400> SEQUENCE: 21

Trp Gly Thr Phe Thr Pro Ser Phe Asp Tyr
1               5                   10

<210> SEQ ID NO 22
<211> LENGTH: 11
<212> TYPE: PRT
<213> ORGANISM: Mus sp.

<400> SEQUENCE: 22

Lys Ala Ser Gln Asp Val Val Thr Ala Val Ala
1               5                   10

<210> SEQ ID NO 23
<211> LENGTH: 7
<212> TYPE: PRT
<213> ORGANISM: Mus sp.

<400> SEQUENCE: 23

Ser Ala Ser His Arg Tyr Thr
1               5

<210> SEQ ID NO 24
<211> LENGTH: 9
<212> TYPE: PRT
<213> ORGANISM: Mus sp.

<400> SEQUENCE: 24

Gln Gln His Tyr Thr Thr Pro Thr Thr
1               5

<210> SEQ ID NO 25
<211> LENGTH: 5
<212> TYPE: PRT
<213> ORGANISM: Mus sp.

<400> SEQUENCE: 25

Ser Tyr Thr Leu Ser
1               5

<210> SEQ ID NO 26
<211> LENGTH: 17
<212> TYPE: PRT
<213> ORGANISM: Mus sp.
```

<400> SEQUENCE: 26

Thr Ile Ser Ile Gly Gly Arg Tyr Thr Tyr Tyr Pro Asp Ser Val Glu
1               5                   10                  15

Gly

<210> SEQ ID NO 27
<211> LENGTH: 8
<212> TYPE: PRT
<213> ORGANISM: Mus sp.

<400> SEQUENCE: 27

Asp Phe Asn Gly Tyr Ser Asp Phe
1               5

<210> SEQ ID NO 28
<211> LENGTH: 11
<212> TYPE: PRT
<213> ORGANISM: Mus sp.

<400> SEQUENCE: 28

Lys Ala Ser Gln Val Val Gly Ser Ala Val Ala
1               5                   10

<210> SEQ ID NO 29
<211> LENGTH: 7
<212> TYPE: PRT
<213> ORGANISM: Mus sp.

<400> SEQUENCE: 29

Trp Ala Ser Thr Arg His Thr
1               5

<210> SEQ ID NO 30
<211> LENGTH: 9
<212> TYPE: PRT
<213> ORGANISM: Mus sp.

<400> SEQUENCE: 30

Gln Gln Tyr Asn Ser Tyr Pro Tyr Thr
1               5

<210> SEQ ID NO 31
<211> LENGTH: 5
<212> TYPE: PRT
<213> ORGANISM: Mus sp.

<400> SEQUENCE: 31

Asn Phe Gly Met His
1               5

<210> SEQ ID NO 32
<211> LENGTH: 17
<212> TYPE: PRT
<213> ORGANISM: Mus sp.

<400> SEQUENCE: 32

Tyr Ile Arg Ser Gly Ser Gly Thr Ile Tyr Tyr Ser Asp Thr Val Lys
1               5                   10                  15

Gly

<210> SEQ ID NO 33
<211> LENGTH: 11

```
<212> TYPE: PRT
<213> ORGANISM: Mus sp.

<400> SEQUENCE: 33

Ser Tyr Tyr Asp Phe Gly Ala Trp Phe Ala Tyr
1               5                   10

<210> SEQ ID NO 34
<211> LENGTH: 11
<212> TYPE: PRT
<213> ORGANISM: Mus sp.

<400> SEQUENCE: 34

Lys Ala Ser Gln Asn Val Gly Thr Asn Val Ala
1               5                   10

<210> SEQ ID NO 35
<211> LENGTH: 7
<212> TYPE: PRT
<213> ORGANISM: Mus sp.

<400> SEQUENCE: 35

Ser Ala Ser Ser Arg Tyr Ser
1               5

<210> SEQ ID NO 36
<211> LENGTH: 9
<212> TYPE: PRT
<213> ORGANISM: Mus sp.

<400> SEQUENCE: 36

Gln Gln Tyr Asn Ser Tyr Pro Leu Thr
1               5

<210> SEQ ID NO 37
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 37 aac att gtg ctg acc caa tct cca gct tct ttg gct gtg tct ctt ggg      48
Asn Ile Val Leu Thr Gln Ser Pro Ala Ser Leu Ala Val Ser Leu Gly
1               5                   10                  15 cag agg gcc acc ata tcc tgc aga gcc agt gaa agt gtt gag att tat      96
Gln Arg Ala Thr Ile Ser Cys Arg Ala Ser Glu Ser Val Glu Ile Tyr
            20                  25                  30 ggc aat ggt ttt atg aac tgg ttc cag cag aaa cca gga cag cca ccc     144
Gly Asn Gly Phe Met Asn Trp Phe Gln Gln Lys Pro Gly Gln Pro Pro
        35                  40                  45 aaa ctc ctc atc tat cgt gca tcc aac cta gaa tct ggg atc cct gcc     192
Lys Leu Leu Ile Tyr Arg Ala Ser Asn Leu Glu Ser Gly Ile Pro Ala
    50                  55                  60 agg ttc agt ggc agt ggg tct agg aca gag ttc acc ctc acc att gat     240
Arg Phe Ser Gly Ser Gly Ser Arg Thr Glu Phe Thr Leu Thr Ile Asp
65                  70                  75                  80 cct gtg gag gct gat gat gtt gca acc tat tac tgt caa caa att aat     288
Pro Val Glu Ala Asp Asp Val Ala Thr Tyr Tyr Cys Gln Gln Ile Asn
                85                  90                  95 gag gat cca ttc acg ttc ggc tcg ggg aca aag ttg gaa ata aaa cgg     336
Glu Asp Pro Phe Thr Phe Gly Ser Gly Thr Lys Leu Glu Ile Lys Arg
            100                 105                 110
```

<210> SEQ ID NO 38
<211> LENGTH: 112
<212> TYPE: PRT
<213> ORGANISM: Mus sp.

<400> SEQUENCE: 38

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ile Tyr
            20                  25                  30

Gly Asn Gly Phe Met Asn Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Glu Phe Thr Leu Thr Ile Asp
65                  70                  75                  80

Pro Val Glu Ala Asp Asp Val Ala Thr Tyr Tyr Cys Gln Gln Ile Asn
                85                  90                  95

Glu Asp Pro Phe Thr Phe Gly Ser Gly Thr Lys Leu Glu Ile Lys Arg
            100                 105                 110
```

<210> SEQ ID NO 39
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 39

```
gac att gta ctg acc caa tct cca gct tct ttg gct gtg tct cta ggg      48
Asp Ile Val Leu Thr Gln Ser Pro Ala Ser Leu Ala Val Ser Leu Gly
1               5                   10                  15 cag agg gcc acc ata tcc tgc aga gcc agt gag agt gtt gct att tat      96
Gln Arg Ala Thr Ile Ser Cys Arg Ala Ser Glu Ser Val Ala Ile Tyr
            20                  25                  30 ggc aat agt ttt ctg aaa tgg ttc cag cag aaa ccg gga cag cca ccc     144
Gly Asn Ser Phe Leu Lys Trp Phe Gln Gln Lys Pro Gly Gln Pro Pro
        35                  40                  45 aaa ctc ctc atc tat cgt gca tcc aac cta gaa tct ggg atc cct gcc     192
Lys Leu Leu Ile Tyr Arg Ala Ser Asn Leu Glu Ser Gly Ile Pro Ala
    50                  55                  60 agg ttc agt ggc agt ggg tct ggg aca gac ttc acc ctc acc att aat     240
Arg Phe Ser Gly Ser Gly Ser Gly Thr Asp Phe Thr Leu Thr Ile Asn
65                  70                  75                  80 cct gtg gag gct gat gat gtt gca acc tat tac tgt cag caa att aat     288
Pro Val Glu Ala Asp Asp Val Ala Thr Tyr Tyr Cys Gln Gln Ile Asn
                85                  90                  95 gag gat ccg tac acg ttc gga ggg ggg acc aag ctg gaa ata aaa cgg     336
Glu Asp Pro Tyr Thr Phe Gly Gly Gly Thr Lys Leu Glu Ile Lys Arg
            100                 105                 110
```

<210> SEQ ID NO 40
<211> LENGTH: 112
<212> TYPE: PRT
<213> ORGANISM: Mus sp.

<400> SEQUENCE: 40

```
Asp Ile Val Leu Thr Gln Ser Pro Ala Ser Leu Ala Val Ser Leu Gly
1               5                   10                  15
```

```
Gln Arg Ala Thr Ile Ser Cys Arg Ala Ser Glu Ser Val Ala Ile Tyr
            20                  25                  30

Gly Asn Ser Phe Leu Lys Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asp Asp Val Ala Thr Tyr Tyr Cys Gln Gln Ile Asn
                85                  90                  95

Glu Asp Pro Tyr Thr Phe Gly Gly Gly Thr Lys Leu Glu Ile Lys Arg
            100                 105                 110

<210> SEQ ID NO 41
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 41 gac att gtg atg gcc cag tct cac aaa ttc atg tcc aca tca gtt gga      48
Asp Ile Val Met Ala Gln Ser His Lys Phe Met Ser Thr Ser Val Gly
 1               5                  10                  15 gac agg gtc agc atc acc tgc aag gcc agt cag gat gtg agt act gtt      96
Asp Arg Val Ser Ile Thr Cys Lys Ala Ser Gln Asp Val Ser Thr Val
            20                  25                  30 gtg gcc tgg tat caa cag aaa cca gga caa tct cct aaa cga ctg att     144
Val Ala Trp Tyr Gln Gln Lys Pro Gly Gln Ser Pro Lys Arg Leu Ile
        35                  40                  45 tac tcg gca tcc tat cgg tat att gga gtc cct gat cgc ttc act ggc     192
Tyr Ser Ala Ser Tyr Arg Tyr Ile Gly Val Pro Asp Arg Phe Thr Gly
 50                  55                  60 agt gga tct ggg acg gat ttc act ttc acc atc agc agt gtg cag gct     240
Ser Gly Ser Gly Thr Asp Phe Thr Phe Thr Ile Ser Ser Val Gln Ala
 65                  70                  75                  80 gaa gac ctg gca gtt tat tac tgt cag caa cat tat agt cct ccg tac     288
Glu Asp Leu Ala Val Tyr Tyr Cys Gln Gln His Tyr Ser Pro Pro Tyr
                85                  90                  95 acg ttc gga ggg ggg acc aag ctg gaa ata aaa cgg                      324
Thr Phe Gly Gly Gly Thr Lys Leu Glu Ile Lys Arg
            100                 105

<210> SEQ ID NO 42
<211> LENGTH: 108
<212> TYPE: PRT
<213> ORGANISM: Mus sp.

<400> SEQUENCE: 42

Asp Ile Val Met Ala Gln Ser His Lys Phe Met Ser Thr Ser Val Gly
 1               5                  10                  15

Asp Arg Val Ser Ile Thr Cys Lys Ala Ser Gln Asp Val Ser Thr Val
            20                  25                  30

Val Ala Trp Tyr Gln Gln Lys Pro Gly Gln Ser Pro Lys Arg Leu Ile
        35                  40                  45

Tyr Ser Ala Ser Tyr Arg Tyr Ile Gly Val Pro Asp Arg Phe Thr Gly
 50                  55                  60

Ser Gly Ser Gly Thr Asp Phe Thr Phe Thr Ile Ser Ser Val Gln Ala
```

```
                        65                  70                  75                  80
Glu Asp Leu Ala Val Tyr Tyr Cys Gln Gln His Tyr Ser Pro Pro Tyr
                    85                  90                  95

Thr Phe Gly Gly Gly Thr Lys Leu Glu Ile Lys Arg
                100                 105
```

<210> SEQ ID NO 43
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 43

```
gac att gtg atg acc cag tct cac aaa ttc ttg tcc aca tca gtt gga        48
Asp Ile Val Met Thr Gln Ser His Lys Phe Leu Ser Thr Ser Val Gly
  1               5                  10                  15 gac agg gtc agt atc acc tgc aag gcc agt cag gat gtg gtt act gct        96
Asp Arg Val Ser Ile Thr Cys Lys Ala Ser Gln Asp Val Val Thr Ala
                 20                  25                  30 gtt gcc tgg ttt caa cag aaa cca gga caa tct cca aaa cta ctg att       144
Val Ala Trp Phe Gln Gln Lys Pro Gly Gln Ser Pro Lys Leu Leu Ile
             35                  40                  45 tat tcg gca tcc cac cgg tac act gga gtc cct gat cgc ttc act ggc       192
Tyr Ser Ala Ser His Arg Tyr Thr Gly Val Pro Asp Arg Phe Thr Gly
         50                  55                  60 agt gga tct ggg aca gat ttc act ttc acc atc atc agt gtg cag gct       240
Ser Gly Ser Gly Thr Asp Phe Thr Phe Thr Ile Ile Ser Val Gln Ala
 65                  70                  75                  80 gaa gac ctg gca gtt tat tac tgt caa caa cat tat act act ccc acg       288
Glu Asp Leu Ala Val Tyr Tyr Cys Gln Gln His Tyr Thr Thr Pro Thr
                 85                  90                  95 acg ttc ggt gga ggc acc aag ctg gac ttc aga cgg                       324
Thr Phe Gly Gly Gly Thr Lys Leu Asp Phe Arg Arg
                100                 105
```

<210> SEQ ID NO 44
<211> LENGTH: 108
<212> TYPE: PRT
<213> ORGANISM: Mus sp.

<400> SEQUENCE: 44

```
Asp Ile Val Met Thr Gln Ser His Lys Phe Leu Ser Thr Ser Val Gly
  1               5                  10                  15

Asp Arg Val Ser Ile Thr Cys Lys Ala Ser Gln Asp Val Val Thr Ala
                 20                  25                  30

Val Ala Trp Phe Gln Gln Lys Pro Gly Gln Ser Pro Lys Leu Leu Ile
             35                  40                  45

Tyr Ser Ala Ser His Arg Tyr Thr Gly Val Pro Asp Arg Phe Thr Gly
         50                  55                  60

Ser Gly Ser Gly Thr Asp Phe Thr Phe Thr Ile Ile Ser Val Gln Ala
 65                  70                  75                  80

Glu Asp Leu Ala Val Tyr Tyr Cys Gln Gln His Tyr Thr Thr Pro Thr
                 85                  90                  95

Thr Phe Gly Gly Gly Thr Lys Leu Asp Phe Arg Arg
                100                 105
```

<210> SEQ ID NO 45
<211> LENGTH: 324

<212> TYPE: DNA
<213> ORGANISM: Mus sp.
<220> FEATURE:
<221> NAME/KEY: CDS
<222> LOCATION: (1)..(324)

<400> SEQUENCE: 45

```
gac act gtg atg acc cag tct cac aaa ttc ata tcc aca tca gtt gga      48
Asp Thr Val Met Thr Gln Ser His Lys Phe Ile Ser Thr Ser Val Gly
1               5                   10                  15 gac agg gtc agc atc acc tgc aag gcc agt cag gtt gtg ggt agt gct      96
Asp Arg Val Ser Ile Thr Cys Lys Ala Ser Gln Val Val Gly Ser Ala
            20                  25                  30 gta gcc tgg tat caa cag aaa cca ggg caa tct cct aaa cta ctg att     144
Val Ala Trp Tyr Gln Gln Lys Pro Gly Gln Ser Pro Lys Leu Leu Ile
        35                  40                  45 tac tgg gca tcc acc cgg cac act gga gtc cct gat cgc ttc aca ggc     192
Tyr Trp Ala Ser Thr Arg His Thr Gly Val Pro Asp Arg Phe Thr Gly
    50                  55                  60 agt gga tct ggg aca gat ttc act ctc acc att agc aat gtg cag tct     240
Ser Gly Ser Gly Thr Asp Phe Thr Leu Thr Ile Ser Asn Val Gln Ser
65                  70                  75                  80 gaa gac ttg gca gat tat ttc tgt cag caa tat aac agc tat ccg tac     288
Glu Asp Leu Ala Asp Tyr Phe Cys Gln Gln Tyr Asn Ser Tyr Pro Tyr
                85                  90                  95 acg ttc gga ggg ggg acc aag ctg gaa ata aaa cgg                     324
Thr Phe Gly Gly Gly Thr Lys Leu Glu Ile Lys Arg
            100                 105
```

<210> SEQ ID NO 46
<211> LENGTH: 108
<212> TYPE: PRT
<213> ORGANISM: Mus sp.

<400> SEQUENCE: 46

```
Asp Thr Val Met Thr Gln Ser His Lys Phe Ile Ser Thr Ser Val Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
            100                 105
```

<210> SEQ ID NO 47
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 47

```
gac att gtg atg acc cag tct caa aaa ttc atg tcc aca tca gta gga      48
Asp Ile Val Met Thr Gln Ser Gln Lys Phe Met Ser Thr Ser Val Gly
1               5                   10                  15
```

```
gac agg gtc agc gtc acc tgc aag gcc agt cag aat gtg ggt act aat       96
Asp Arg Val Ser Val Thr Cys Lys Ala Ser Gln Asn Val Gly Thr Asn
             20                  25                  30 gtt gcc tgg tat caa cac aaa cca gga caa tcc cct aaa ata atg att      144
Val Ala Trp Tyr Gln His Lys Pro Gly Gln Ser Pro Lys Ile Met Ile
         35                  40                  45 tat tcg gcg tcc tcc cgg tac agt gga gtc cct gat cgc ttc aca ggc      192
Tyr Ser Ala Ser Ser Arg Tyr Ser Gly Val Pro Asp Arg Phe Thr Gly
     50                  55                  60 agt gga tct ggg aca ctt ttc act ctc acc atc aac aat gtg cag tct      240
Ser Gly Ser Gly Thr Leu Phe Thr Leu Thr Ile Asn Asn Val Gln Ser
 65                  70                  75                  80 gaa gac ttg gca gag tat ttc tgt cag caa tat aac agc tat cct ctc      288
Glu Asp Leu Ala Glu Tyr Phe Cys Gln Gln Tyr Asn Ser Tyr Pro Leu
                 85                  90                  95 acg ttc ggc tcg ggg aca aag ttg gaa ata aaa cgg                      324
Thr Phe Gly Ser Gly Thr Lys Leu Glu Ile Lys Arg
             100                 105

<210> SEQ ID NO 48
<211> LENGTH: 108
<212> TYPE: PRT
<213> ORGANISM: Mus sp.

<400> SEQUENCE: 48

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
             20                  25                  30

Val Ala Trp Tyr Gln His Lys Pro Gly Gln Ser Pro Lys Ile Met Ile
         35                  40                  45

Tyr Ser Ala Ser Ser Arg Tyr Ser Gly Val Pro Asp Arg Phe Thr Gly
     50                  55                  60

Ser Gly Ser Gly Thr Leu Phe Thr Leu Thr Ile Asn Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Ser Gly Thr Lys Leu Glu Ile Lys Arg
             100                 105

<210> SEQ ID NO 49
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 49 cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15 aca gtc aag atc tcc tgc aag gct tct ggg tat acc ctc aca agc tac       96
Thr Val Lys Ile Ser Cys Lys Ala Ser Gly Tyr Thr Leu Thr Ser Tyr
             20                  25                  30 gga atg aac tgg gtg aag cag gct cca gga aag ggt tta aag tgg atg      144
Gly Met Asn Trp Val Lys Gln Ala Pro Gly Lys Gly Leu Lys Trp Met
         35                  40                  45 ggc tgg ata aac acc tac act gga gaa cca aca tat gct gat gac ttt      192
Gly Trp Ile Asn Thr Tyr Thr Gly Glu Pro Thr Tyr Ala Asp Asp Phe
```

```
aag gga cgt ttt gcc ttc tct ttg gaa acc tct gcc agc act gcc ttt      240
Lys Gly Arg Phe Ala Phe Ser Leu Glu Thr Ser Ala Ser Thr Ala Phe
 65                  70                  75                  80 ttg cag atc aac aac ctc aaa aat gag gac acg gct aca tat ttc tgt      288
Leu Gln Ile Asn Asn Leu Lys Asn Glu Asp Thr Ala Thr Tyr Phe Cys
                 85                  90                  95 gta aga cgc ggg ttt gct tac tgg ggc caa ggg act ctg gtc act gtc      336
Val Arg Arg Gly Phe Ala Tyr Trp Gly Gln Gly Thr Leu Val Thr Val
            100                 105                 110 tct gca                                                              342
Ser Ala <210> SEQ ID NO 50
<211> LENGTH: 114
<212> TYPE: PRT
<213> ORGANISM: Mus sp.

<400> SEQUENCE: 50

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Leu Thr Ser Tyr
             20                  25                  30

Gly Met Asn Trp Val Lys Gln Ala Pro Gly Lys Gly Leu Lys Trp Met
         35                  40                  45

Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                 85                  90                  95

Val Arg Arg Gly Phe Ala Tyr Trp Gly Gln Gly Thr Leu Val Thr Val
            100                 105                 110

Ser Ala

<210> SEQ ID NO 51
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 51 cag atc cag ttg gtg cag tct gga cct gag ctg aag aag cct gga gag       48
Gln Ile Gln Leu Val Gln Ser Gly Pro Glu Leu Lys Lys Pro Gly Glu
 1               5                  10                  15 aca gtc aag atc tcc tgc aag gct tct ggg tat acc ttc aca aac tct       96
Thr Val Lys Ile Ser Cys Lys Ala Ser Gly Tyr Thr Phe Thr Asn Ser
             20                  25                  30 gga atg aac tgg gtg aag cag gct cca gga aag ggt tta aag tgg atg      144
Gly Met Asn Trp Val Lys Gln Ala Pro Gly Lys Gly Leu Lys Trp Met
         35                  40                  45 ggc tgg ata aac acc tac act gga gag ccg aca tat gct gat gac ttc      192
Gly Trp Ile Asn Thr Tyr Thr Gly Glu Pro Thr Tyr Ala Asp Asp Phe
     50                  55                  60 aag gga cgg ttt gcc ttc tct ttg gaa acc tct gcc agc tct gcc tat      240
Lys Gly Arg Phe Ala Phe Ser Leu Glu Thr Ser Ala Ser Ser Ala Tyr
 65                  70                  75                  80
```

```
ttg cag atc agt aac ctc aaa aat gag gac acg gct aca tat ttc tgt    288
Leu Gln Ile Ser Asn Leu Lys Asn Glu Asp Thr Ala Thr Tyr Phe Cys
                85                  90                  95 gca aga agg ggt ttt gtt tac tgg ggc caa ggg act ctg gta act gtc    336
Ala Arg Arg Gly Phe Val Tyr Trp Gly Gln Gly Thr Leu Val Thr Val
            100                 105                 110 tct gca                                                            342
Ser Ala
```

<210> SEQ ID NO 52
<211> LENGTH: 114
<212> TYPE: PRT
<213> ORGANISM: Mus sp.

<400> SEQUENCE: 52

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Ser Asn Leu Lys Asn Glu Asp Thr Ala Thr Tyr Phe Cys
                85                  90                  95

Ala Arg Arg Gly Phe Val Tyr Trp Gly Gln Gly Thr Leu Val Thr Val
            100                 105                 110

Ser Ala
```

<210> SEQ ID NO 53
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 53

```
cag gtt cag ctc cag cag tct ggg gct gag ctg gca aga cct ggg act    48
Gln Val Gln Leu Gln Gln Ser Gly Ala Glu Leu Ala Arg Pro Gly Thr
1               5                   10                  15 tca gtg aag ttg tcc tgt aag gct tct ggc tac acc ttt act gac tac    96
Ser Val Lys Leu Ser Cys Lys Ala Ser Gly Tyr Thr Phe Thr Asp Tyr
            20                  25                  30 tgg atg cag tgg gta aaa cag agg cct gga cag ggt ctg gag tgg att    144
Trp Met Gln Trp Val Lys Gln Arg Pro Gly Gln Gly Leu Glu Trp Ile
        35                  40                  45 ggg act att tat cct gga gat ggt gat act ggg tac gct cag aag ttc    192
Gly Thr Ile Tyr Pro Gly Asp Gly Asp Thr Gly Tyr Ala Gln Lys Phe
    50                  55                  60 aag ggc aag gcc aca ttg act gcg gat aaa tcc tcc aaa aca gtc tac    240
Lys Gly Lys Ala Thr Leu Thr Ala Asp Lys Ser Ser Lys Thr Val Tyr
65                  70                  75                  80 atg cac ctc agc agt ttg gct tct gag gac tct gcg gtc tat tac tgt    288
Met His Leu Ser Ser Leu Ala Ser Glu Asp Ser Ala Val Tyr Tyr Cys
                85                  90                  95 gca aga ggg gat tac tac ggt agt aat tct ttg gac tat tgg ggt caa    336
Ala Arg Gly Asp Tyr Tyr Gly Ser Asn Ser Leu Asp Tyr Trp Gly Gln
```

```
                   100                 105                 110
gga acc tca gtc acc gtc tcc tca                                             360
Gly Thr Ser Val Thr Val Ser Ser
        115                 120

<210> SEQ ID NO 54
<211> LENGTH: 120
<212> TYPE: PRT
<213> ORGANISM: Mus sp.

<400> SEQUENCE: 54

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Lys Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 55
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 55 cag gtc cag tta cag caa tct gga cct gaa ctg gtg agg cct ggg gcc           48
Gln Val Gln Leu Gln Gln Ser Gly Pro Glu Leu Val Arg Pro Gly Ala
1               5                   10                  15 tca gtg aag att tcc tgc aaa act tct ggc tac gca ttc agt ggc tcc           96
Ser Val Lys Ile Ser Cys Lys Thr Ser Gly Tyr Ala Phe Ser Gly Ser
            20                  25                  30 tgg atg aac tgg gtg aag cag agg cct gga cag ggt cta gag tgg att          144
Trp Met Asn Trp Val Lys Gln Arg Pro Gly Gln Gly Leu Glu Trp Ile
        35                  40                  45 gga cgg att tat ccg gga gat gga gat atc att tac aat ggg aat ttc          192
Gly Arg Ile Tyr Pro Gly Asp Gly Asp Ile Ile Tyr Asn Gly Asn Phe
    50                  55                  60 agg gac aag gtc aca ctg tct gca gac aaa tcc tcc aac aca gcc tac          240
Arg Asp Lys Val Thr Leu Ser Ala Asp Lys Ser Ser Asn Thr Ala Tyr
65                  70                  75                  80 atg cag ctc agc agc ctg acc tct gtg gac tct gcg gtc tat ttt tgt          288
Met Gln Leu Ser Ser Leu Thr Ser Val Asp Ser Ala Val Tyr Phe Cys
                85                  90                  95 tcg aga tgg ggg aca ttt acg ccg agt ttt gac tat tgg ggc caa ggc          336
Ser Arg Trp Gly Thr Phe Thr Pro Ser Phe Asp Tyr Trp Gly Gln Gly
            100                 105                 110 acc act ctc aca gtc tcc tca                                              357
Thr Thr Leu Thr Val Ser Ser
```

<210> SEQ ID NO 56
<211> LENGTH: 119
<212> TYPE: PRT
<213> ORGANISM: Mus sp.

<400> SEQUENCE: 56

```
Gln Val Gln Leu Gln Gln Ser Gly Pro Glu Leu Val Arg Pro Gly Ala
1               5                   10                  15
Ser Val Lys Ile Ser Cys Lys Thr Ser Gly Tyr Ala Phe Ser Gly Ser
                20                  25                  30
Trp Met Asn Trp Val Lys Gln Arg Pro Gly Gln Gly Leu Glu Trp Ile
            35                  40                  45
Gly Arg Ile Tyr Pro Gly Asp Gly Asp Ile Ile Tyr Asn Gly Asn Phe
        50                  55                  60
Arg Asp Lys Val Thr Leu Ser Ala Asp Lys Ser Ser Asn Thr Ala Tyr
65                  70                  75                  80
Met Gln Leu Ser Ser Leu Thr Ser Val Asp Ser Ala Val Tyr Phe Cys
                85                  90                  95
Ser Arg Trp Gly Thr Phe Thr Pro Ser Phe Asp Tyr Trp Gly Gln Gly
            100                 105                 110
Thr Thr Leu Thr Val Ser Ser
        115
```

<210> SEQ ID NO 57
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 57

```
gac gtg aag ctg gtg gag tct ggg gga ggc tta gtg aag cct gga ggg     48
Asp Val Lys Leu Val Glu Ser Gly Gly Gly Leu Val Lys Pro Gly Gly
1               5                   10                  15 tcc ctg aaa ctc tcc tgt gaa gcc tct gga ttc act ttc agt agc tat     96
Ser Leu Lys Leu Ser Cys Glu Ala Ser Gly Phe Thr Phe Ser Ser Tyr
                20                  25                  30 acc ctg tct tgg gtt cgc cag act ccg gag acg agg ctg gag tgg gtc    144
Thr Leu Ser Trp Val Arg Gln Thr Pro Glu Thr Arg Leu Glu Trp Val
            35                  40                  45 gca acc att agt att ggt ggt cgc tac acc tat tat cca gac agt gtg    192
Ala Thr Ile Ser Ile Gly Gly Arg Tyr Thr Tyr Tyr Pro Asp Ser Val
        50                  55                  60 gag ggc cga ttc acc atc tcc aga gac aat gcc aag aac acc ctg tac    240
Glu Gly Arg Phe Thr Ile Ser Arg Asp Asn Ala Lys Asn Thr Leu Tyr
65                  70                  75                  80 ctg caa atg aac agt ctg aag tct gag gac aca gcc atg tat tac tgt    288
Leu Gln Met Asn Ser Leu Lys Ser Glu Asp Thr Ala Met Tyr Tyr Cys
                85                  90                  95 aca aga gat ttt aat ggt tac tct gac ttc tgg ggc caa ggc acc act    336
Thr Arg Asp Phe Asn Gly Tyr Ser Asp Phe Trp Gly Gln Gly Thr Thr
            100                 105                 110 ctc aca gtc tcc tca                                                 351
Leu Thr Val Ser Ser
        115
```

<210> SEQ ID NO 58

<211> LENGTH: 117
<212> TYPE: PRT
<213> ORGANISM: Mus sp.

<400> SEQUENCE: 58

Asp Val Lys Leu Val Glu Ser Gly Gly Gly Leu Val Lys Pro Gly Gly
1               5                   10                  15
Ser Leu Lys Leu Ser Cys Glu Ala Ser Gly Phe Thr Phe Ser Ser Tyr
            20                  25                  30
Thr Leu Ser Trp Val Arg Gln Thr Pro Glu Thr Arg Leu Glu Trp Val
        35                  40                  45
Ala Thr Ile Ser Ile Gly Gly Arg Tyr Thr Tyr Tyr Pro Asp Ser Val
    50                  55                  60
Glu Gly Arg Phe Thr Ile Ser Arg Asp Asn Ala Lys Asn Thr Leu Tyr
65                  70                  75                  80
Leu Gln Met Asn Ser Leu Lys Ser Glu Asp Thr Ala Met Tyr Tyr Cys
                85                  90                  95
Thr Arg Asp Phe Asn Gly Tyr Ser Asp Phe Trp Gly Gly Thr
            100                 105                 110
Leu Thr Val Ser Ser
        115

<210> SEQ ID NO 59
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 59 aat gta cag ctg gta gag tct ggg gga ggc tta gtg cag cct gga ggg      48
Asn Val Gln Leu Val Glu Ser Gly Gly Gly Leu Val Gln Pro Gly Gly
1               5                   10                  15 tcc cgg aaa ctc tcc tgt gca gcc tct gga ttc act ttc agt aac ttt      96
Ser Arg Lys Leu Ser Cys Ala Ala Ser Gly Phe Thr Phe Ser Asn Phe
            20                  25                  30 gga atg cac tgg gtt cgt cag gct cca gag aag ggt ctg gag tgg gtc     144
Gly Met His Trp Val Arg Gln Ala Pro Glu Lys Gly Leu Glu Trp Val
        35                  40                  45 gca tac att cgt agt ggc agt ggt acc atc tac tat tca gac aca gtg     192
Ala Tyr Ile Arg Ser Gly Ser Gly Thr Ile Tyr Tyr Ser Asp Thr Val
    50                  55                  60 aag ggc cga ttc acc atc tcc aga gac aat ccc aag aac acc ctg ttc     240
Lys Gly Arg Phe Thr Ile Ser Arg Asp Asn Pro Lys Asn Thr Leu Phe
65                  70                  75                  80 ctg caa atg acc agt cta agg tct gag gac acg gcc atg tat tac tgt     288
Leu Gln Met Thr Ser Leu Arg Ser Glu Asp Thr Ala Met Tyr Tyr Cys
                85                  90                  95 gca aga tcc tac tat gat ttc ggg gcc tgg ttt gct tac tgg ggc caa     336
Ala Arg Ser Tyr Tyr Asp Phe Gly Ala Trp Phe Ala Tyr Trp Gly Gln
            100                 105                 110 ggg act ctg gtc act gtc tct gca                                     360
Gly Thr Leu Val Thr Val Ser Ala
        115                 120

<210> SEQ ID NO 60
<211> LENGTH: 120
<212> TYPE: PRT
<213> ORGANISM: Mus sp.

<400> SEQUENCE: 60

Asn Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Arg Ser Gly Ser Gly Thr Ile Tyr Tyr Ser Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Tyr Tyr Asp Phe Gly Ala Trp Phe Ala Tyr Trp Gly Gln
            100                 105                 110

Gly Thr Leu Val Thr Val Ser Ala
        115                 120

<210> SEQ ID NO 61
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 61 gat atc gta atg acc cag tcc cac ctg agt atg agt acc tcc ctg gga       48
Asp Ile Val Met Thr Gln Ser His Leu Ser Met Ser Thr Ser Leu Gly
1               5                   10                  15 gat cct gtg tca atc act tgc aag gcc tca cag gat gtg agc acc gtc       96
Asp Pro Val Ser Ile Thr Cys Lys Ala Ser Gln Asp Val Ser Thr Val
            20                  25                  30 gtt gct tgg tat cag cag aag ccc ggg caa tca ccc aga cgt ctc atc      144
Val Ala Trp Tyr Gln Gln Lys Pro Gly Gln Ser Pro Arg Arg Leu Ile
        35                  40                  45 tac tca gca tca tac cgt tac atc ggg gtg cct gac cga ttt act ggc      192
Tyr Ser Ala Ser Tyr Arg Tyr Ile Gly Val Pro Asp Arg Phe Thr Gly
    50                  55                  60 tct ggc gct ggc aca gat ttc acc ttt aca att agt tcc gtc cag gcc      240
Ser Gly Ala Gly Thr Asp Phe Thr Phe Thr Ile Ser Ser Val Gln Ala
65                  70                  75                  80 gaa gac ctg gcc gtg tac tac tgc cag cag cac tac agt ccc cca tac      288
Glu Asp Leu Ala Val Tyr Tyr Cys Gln Gln His Tyr Ser Pro Pro Tyr
                85                  90                  95 act ttc ggg gga ggg act aag ctc gaa atc aaa cgt                      324
Thr Phe Gly Gly Gly Thr Lys Leu Glu Ile Lys Arg
            100                 105

<210> SEQ ID NO 62
<211> LENGTH: 108
<212> TYPE: PRT
<213> ORGANISM: Homo sapiens

<400> SEQUENCE: 62

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Leu Ile
            35                  40                  45

Tyr Ser Ala Ser Tyr Arg Tyr Ile Gly Val Pro Asp Arg Phe Thr Gly
 50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys Arg
            100                 105

<210> SEQ ID NO 63
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 63 gac att gtt atg gct caa agc cat ctg tct atg agc aca tct ctg gga    48
Asp Ile Val Met Ala Gln Ser His Leu Ser Met Ser Thr Ser Leu Gly
 1               5                  10                  15 gat cct gtg tcc atc act tgc aaa gcc agt caa gac gtg tct aca gtt    96
Asp Pro Val Ser Ile Thr Cys Lys Ala Ser Gln Asp Val Ser Thr Val
                 20                  25                  30 gtt gca tgg tat caa cag aag cca ggc cag tca ccc aga cgg ctc att   144
Val Ala Trp Tyr Gln Gln Lys Pro Gly Gln Ser Pro Arg Arg Leu Ile
             35                  40                  45 tac tca gct tct tac cga tac atc ggg gtc cct gac aga ttt aca ggt   192
Tyr Ser Ala Ser Tyr Arg Tyr Ile Gly Val Pro Asp Arg Phe Thr Gly
 50                  55                  60 agt ggg gcc ggt act gac ttc act ttt act atc tca tcc gta caa gcc   240
Ser Gly Ala Gly Thr Asp Phe Thr Phe Thr Ile Ser Ser Val Gln Ala
 65                  70                  75                  80 gaa gac ctg gca gta tat tac tgc cag caa cat tat tcc cca ccc tac   288
Glu Asp Leu Ala Val Tyr Tyr Cys Gln Gln His Tyr Ser Pro Pro Tyr
                 85                  90                  95 aca ttc ggc ggg ggt act aag ctg gaa att aaa cgt                   324
Thr Phe Gly Gly Gly Thr Lys Leu Glu Ile Lys Arg
            100                 105

<210> SEQ ID NO 64
<211> LENGTH: 108
<212> TYPE: PRT
<213> ORGANISM: Homo sapiens

<400> SEQUENCE: 64

Asp Ile Val Met Ala Gln Ser His Leu Ser Met Ser Thr Ser Leu Gly
 1               5                  10                  15

Asp Pro Val Ser Ile Thr Cys Lys Ala Ser Gln Asp Val Ser Thr Val
                 20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
 50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

```
Thr Phe Gly Gly Gly Thr Lys Leu Glu Ile Lys Arg
            100                 105
```

<210> SEQ ID NO 65
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 65

```
cag gta cag ctc gtt cag tcc ggc gcc gag gta gct aag cct ggt act       48
Gln Val Gln Leu Val Gln Ser Gly Ala Glu Val Ala Lys Pro Gly Thr
1               5                   10                  15 tcc gta aaa ttg tcc tgt aag gct tcc ggg tac aca ttt aca gac tac       96
Ser Val Lys Leu Ser Cys Lys Ala Ser Gly Tyr Thr Phe Thr Asp Tyr
            20                  25                  30 tgg atg cag tgg gta aaa cag cgg cca ggt cag ggc ctg gag tgg att      144
Trp Met Gln Trp Val Lys Gln Arg Pro Gly Gln Gly Leu Glu Trp Ile
        35                  40                  45 gga aca ata tat ccc ggc gac ggc gac aca ggc tat gcc cag aag ttt      192
Gly Thr Ile Tyr Pro Gly Asp Gly Asp Thr Gly Tyr Ala Gln Lys Phe
    50                  55                  60 caa ggc aag gca acc ctt act gct gat aaa tct tcc aag act gtc tac      240
Gln Gly Lys Ala Thr Leu Thr Ala Asp Lys Ser Ser Lys Thr Val Tyr
65                  70                  75                  80 atg cat ctg tct tcc ttg gca tct gag gat agc gct gtc tat tac tgt      288
Met His Leu Ser Ser Leu Ala Ser Glu Asp Ser Ala Val Tyr Tyr Cys
                85                  90                  95 gct agg ggg gac tac tat ggg tca aat tcc ctg gat tac tgg ggc cag      336
Ala Arg Gly Asp Tyr Tyr Gly Ser Asn Ser Leu Asp Tyr Trp Gly Gln
            100                 105                 110 ggc acc agt gtc acc gtg agc agc                                      360
Gly Thr Ser Val Thr Val Ser Ser
        115                 120
```

<210> SEQ ID NO 66
<211> LENGTH: 120
<212> TYPE: PRT
<213> ORGANISM: Homo sapiens

<400> SEQUENCE: 66

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120
```

<210> SEQ ID NO 67
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 67

| | | | | | | | | | | | | | | | | |
|---|---|---|---|---|---|---|---|---|---|---|---|---|---|---|---|---|
| gac | acc | gtg | atg | acc | cag | tcc | ccc | tcc | acc | atc | tcc | acc | tct | gtg | ggc | 48 |
| Asp | Thr | Val | Met | Thr | Gln | Ser | Pro | Ser | Thr | Ile | Ser | Thr | Ser | Val | Gly | |
| 1 | | | | 5 | | | | | 10 | | | | | 15 | | |
| gac | cgg | gtg | tcc | atc | acc | tgt | aag | gcc | tcc | cag | gtg | gtg | ggc | tcc | gcc | 96 |
| Asp | Arg | Val | Ser | Ile | Thr | Cys | Lys | Ala | Ser | Gln | Val | Val | Gly | Ser | Ala | |
| | | | 20 | | | | | 25 | | | | | 30 | | | |
| gtg | gcc | tgg | tat | cag | cag | aag | cct | ggc | cag | tcc | cct | aag | ctg | ctg | atc | 144 |
| Val | Ala | Trp | Tyr | Gln | Gln | Lys | Pro | Gly | Gln | Ser | Pro | Lys | Leu | Leu | Ile | |
| | | 35 | | | | | 40 | | | | | 45 | | | | |
| tac | tgg | gcc | tcc | acc | cgg | cat | acc | ggc | gtg | cct | gac | cgg | ttc | acc | ggc | 192 |
| Tyr | Trp | Ala | Ser | Thr | Arg | His | Thr | Gly | Val | Pro | Asp | Arg | Phe | Thr | Gly | |
| | 50 | | | | | 55 | | | | | 60 | | | | | |
| tcc | ggc | agc | ggc | acc | gac | ttc | acc | ctg | acc | atc | tcc | aac | gtg | cag | tcc | 240 |
| Ser | Gly | Ser | Gly | Thr | Asp | Phe | Thr | Leu | Thr | Ile | Ser | Asn | Val | Gln | Ser | |
| 65 | | | | | 70 | | | | | 75 | | | | | 80 | |
| gac | gac | ctg | gcc | gac | tac | ttc | tgc | cag | cag | tac | aac | tcc | tac | cct | tac | 288 |
| Asp | Asp | Leu | Ala | Asp | Tyr | Phe | Cys | Gln | Gln | Tyr | Asn | Ser | Tyr | Pro | Tyr | |
| | | | 85 | | | | | 90 | | | | | 95 | | | |
| acc | ttt | ggc | ggc | gga | aca | aag | ctg | gag | atc | aag | cgt | | | | | 324 |
| Thr | Phe | Gly | Gly | Gly | Thr | Lys | Leu | Glu | Ile | Lys | Arg | | | | | |
| | | 100 | | | | | 105 | | | | | | | | | |

<210> SEQ ID NO 68
<211> LENGTH: 108
<212> TYPE: PRT
<213> ORGANISM: Homo sapiens

<400> SEQUENCE: 68

Asp Thr Val Met Thr Gln Ser Pro Ser Thr Ile Ser Thr Ser Val Gly
1               5                   10                  15

Asp Arg Val Ser Ile Thr Cys Lys Ala Ser Gln Val Val Gly Ser Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Asp Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
                100                 105

<210> SEQ ID NO 69
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 69

-continued

```
gac acc gtg atg acc cag tcc ccc tcc tcc atc tcc acc tcc atc ggc    48
Asp Thr Val Met Thr Gln Ser Pro Ser Ser Ile Ser Thr Ser Ile Gly
1               5                   10                  15 gac cgg gtg tcc atc acc tgt aag gcc tcc cag gtg gtg ggc tcc gcc    96
Asp Arg Val Ser Ile Thr Cys Lys Ala Ser Gln Val Val Gly Ser Ala
                20                  25                  30 gtg gcc tgg tat cag cag aag cct ggc cag tcc cct aag ctg ctg atc   144
Val Ala Trp Tyr Gln Gln Lys Pro Gly Gln Ser Pro Lys Leu Leu Ile
            35                  40                  45 tac tgg gcc tcc acc cgg cat acc ggc gtg cct gcc cgg ttc acc ggc   192
Tyr Trp Ala Ser Thr Arg His Thr Gly Val Pro Ala Arg Phe Thr Gly
    50                  55                  60 tcc ggc agc ggc acc gac ttc acc ctg acc atc tcc aac gtg cag tcc   240
Ser Gly Ser Gly Thr Asp Phe Thr Leu Thr Ile Ser Asn Val Gln Ser
65                  70                  75                  80 gag gac ctg gcc gac tac ttc tgc cag cag tac aac tcc tac cct tac   288
Glu Asp Leu Ala Asp Tyr Phe Cys Gln Gln Tyr Asn Ser Tyr Pro Tyr
                85                  90                  95 acc ttt ggc ggc gga aca aag ctg gag atc aag cgt                   324
Thr Phe Gly Gly Gly Thr Lys Leu Glu Ile Lys Arg
                100                 105
```

<210> SEQ ID NO 70
<211> LENGTH: 108
<212> TYPE: PRT
<213> ORGANISM: Homo sapiens

<400> SEQUENCE: 70

```
Asp Thr Val Met Thr Gln Ser Pro Ser Ser Ile Ser Thr Ser Ile Gly
1               5                   10                  15

Asp Arg Val Ser Ile Thr Cys Lys Ala Ser Gln Val Val Gly Ser Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
                100                 105
```

<210> SEQ ID NO 71
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 71

```
gag gtg cag ctg gtg gag tct ggc ggc gga ctg gtg aag cct ggc ggc    48
Glu Val Gln Leu Val Glu Ser Gly Gly Gly Leu Val Lys Pro Gly Gly
1               5                   10                  15 tcc ctg agg ctg tcc tgt gag gcc tcc ggc ttc acc ttc tcc tcc tac    96
Ser Leu Arg Leu Ser Cys Glu Ala Ser Gly Phe Thr Phe Ser Ser Tyr
                20                  25                  30 acc ctg tcc tgg gtg agg cag acc cct ggc aag ggc ctg gag tgg gtg   144
Thr Leu Ser Trp Val Arg Gln Thr Pro Gly Lys Gly Leu Glu Trp Val
            35                  40                  45
```

-continued

```
gcc acc atc tcc atc ggc ggc agg tac acc tac tac cct gac tcc gtg      192
Ala Thr Ile Ser Ile Gly Gly Arg Tyr Thr Tyr Tyr Pro Asp Ser Val
 50                  55                  60 aag ggc cgg ttc acc atc tcc cgg gac aac gcc aag aac acc ctg tac      240
Lys Gly Arg Phe Thr Ile Ser Arg Asp Asn Ala Lys Asn Thr Leu Tyr
 65                  70                  75                  80 ctg cag atg aac tcc ctg aag tcc gag gac acc gcc atg tac tac tgt      288
Leu Gln Met Asn Ser Leu Lys Ser Glu Asp Thr Ala Met Tyr Tyr Cys
                 85                  90                  95 acc cgg gac ttc aac ggc tac tcc gac ttc tgg ggc cag ggc acc aca      336
Thr Arg Asp Phe Asn Gly Tyr Ser Asp Phe Trp Gly Gln Gly Thr Thr
             100                 105                 110 ctg acc gtg tcc tcc                                                   351
Leu Thr Val Ser Ser
        115

<210> SEQ ID NO 72
<211> LENGTH: 117
<212> TYPE: PRT
<213> ORGANISM: Homo sapiens

<400> SEQUENCE: 72

Glu Val Gln Leu Val Glu Ser Gly Gly Gly Leu Val Lys Pro Gly Gly
 1               5                  10                  15

Ser Leu Arg Leu Ser Cys Glu Ala Ser Gly Phe Thr Phe Ser Ser Tyr
             20                  25                  30

Thr Leu Ser Trp Val Arg Gln Thr Pro Gly Lys Gly Leu Glu Trp Val
         35                  40                  45

Ala Thr Ile Ser Ile Gly Gly Arg Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Thr Arg Asp Phe Asn Gly Tyr Ser Asp Phe Trp Gly Gln Gly Thr Thr
             100                 105                 110

Leu Thr Val Ser Ser
        115

<210> SEQ ID NO 73
<211> LENGTH: 36
<212> TYPE: DNA
<213> ORGANISM: Mus sp.

<400> SEQUENCE: 73
ggaggatcca tagacagatg ggggtgtcgt tttggc                                36

<210> SEQ ID NO 74
<211> LENGTH: 32
<212> TYPE: DNA
<213> ORGANISM: Mus sp.

<400> SEQUENCE: 74
ggaggatccc ttgaccaggc atcctagagt ca                                    32

<210> SEQ ID NO 75
<211> LENGTH: 32
<212> TYPE: DNA
<213> ORGANISM: Mus sp.
<220> FEATURE:
```

```
<221> NAME/KEY: misc_feature
<222> LOCATION: (1)..(32)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 75
cttccggaat tcsargtnma gctgsagsag tc                                       32

<210> SEQ ID NO 76
<211> LENGTH: 35
<212> TYPE: DNA
<213> ORGANISM: Mus sp.
<220> FEATURE:
<221> NAME/KEY: misc_feature
<222> LOCATION: (1)..(35)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 76
cttccggaat tcsargtnma gctgsagsag tcwgg                                    35

<210> SEQ ID NO 77
<211> LENGTH: 31
<212> TYPE: DNA
<213> ORGANISM: Mus sp.
<220> FEATURE:
<221> NAME/KEY: misc_feature
<222> LOCATION: (1)..(31)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 77
ggagctcgay attgtgmtsa cmcarwctmc a                                        31

<210> SEQ ID NO 78
<211> LENGTH: 46
<212> TYPE: DNA
<213> ORGANISM: Mus sp.

<400> SEQUENCE: 78
tatagagctc aagcttggat ggtgggaaga tggatacagt tggtgc                        46

<210> SEQ ID NO 79
<211> LENGTH: 21
<212> TYPE: DNA
<213> ORGANISM: Mus sp.

<400> SEQUENCE: 79
atggagtcac agattcaggt c                                                   21

<210> SEQ ID NO 80
<211> LENGTH: 32
<212> TYPE: DNA
<213> ORGANISM: Mus sp.

<400> SEQUENCE: 80
ttttgaattc cagtaacttc aggtgtccac tc                                       32

<210> SEQ ID NO 81
<211> LENGTH: 17
<212> TYPE: PRT
<213> ORGANISM: Artificial
<220> FEATURE:
<223> OTHER INFORMATION: humanised

<400> SEQUENCE: 81
```

```
Thr Ile Tyr Pro Gly Asp Gly Asp Thr Gly Tyr Ala Gln Lys Phe Gln
1               5                   10                  15
Gly
```

ANTITUMORS COMBINATIONS CONTAINING ANTIBODIES RECOGNIZING SPECIFICALLY CD38 AND BORTEZOMIB

RELATED APPLICATIONS

This application is a 35 U.S.C. §371 filing of International Application No. PCT/EP2011/072228, filed Dec. 8, 2011, which claims priority to European Patent Application No. 10306395.4, filed on Dec. 10, 2010. The entire contents of which incorporated herein by reference.

The present invention relates to combinations of monoclonal antibodies directed against CD38 and bortezomib which are therapeutically useful in the treatment of neoplastic diseases.

CD38 is a 45 kD type II transmembrane glycoprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. CD38 is up regulated and has been implicated in many hematopoietic malignancies.

Monoclonal antibodies 38SB13, 38SB18, 38SB19, 38SB30, 38SB31, and 38SB39, which specifically recognize CD38, are described in PCT application WO2008/047242, herein incorporated by reference in its entirety. Said anti-CD38 antibodies are capable of killing $CD38^+$ cells by three different cytotoxic mechanisms, induction of apoptosis, antibody-dependent cell-mediated cytotoxicity (ADCC), and complement-dependent cytoxicity (CDC). In addition, these antibodies are able to directly induce apoptosis of $CD38^+$ cells, even without the presence of stroma cells or stroma-derived cytokines.

The term "antibody" is used herein in the broadest sense and specifically covers monoclonal antibodies (including full length monoclonal antibodies) of any isotype such as IgG, IgM, IgA, IgD and IgE, polyclonal antibodies, multispecific antibodies, chimeric antibodies, and antibody fragments. A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions outside of the CDRs are called the "framework regions".

As used herein, "$V_H$" or "VH" refers to the variable region of an immunoglobulin heavy chain of an antibody, including the heavy chain of an Fv, scFv, dsFv, Fab, Fab' or F(ab')2 fragment. Reference to "$V_L$" or "VL" refers to the variable region of the immunoglobulin light chain of an antibody, including the light chain of an Fv, scFv, dsFv, Fab, Fab' or F(ab')2 fragment.

The 38SB13 antibody comprises at least one heavy chain having an amino acid sequence consisting of SEQ ID NO: 50 and at least one light chain having an amino acid sequence consisting of SEQ ID NO: 38, said heavy chain comprising three sequential CDRs having amino acid sequences consisting of SEQ ID NOS: 1, 2, and 3, and said light chain comprising three sequential CDRs having amino acid sequences consisting of SEQ ID NOS: 4, 5, and 6.

The 38SB18 antibody comprises at least one heavy chain having an amino acid sequence consisting of SEQ ID NO: 52 and at least one light chain having an amino acid sequence consisting of SEQ ID NO: 40, said heavy chain comprising three sequential CDRs having amino acid sequences consisting of SEQ ID NOS: 7, 8, and 9, and said light chain comprising three sequential CDRs having amino acid sequences consisting of SEQ ID NOS: 10, 11, and 12.

The 38SB19 antibody comprises at least one heavy chain having an amino acid sequence consisting of SEQ ID NO: 54 and at least one light chain having an amino acid sequence consisting of SEQ ID NO: 42, said heavy chain comprising three sequential CDRs having amino acid sequences consisting of SEQ ID NOS: 13, 14 (or 81), and 15, and said light chain comprising three sequential CDRs having amino acid sequences consisting of SEQ ID NOS: 16, 17, and 18.

The 38SB30 antibody comprises at least one heavy chain having an amino acid sequence consisting of SEQ ID NO: 56 and at least one light chain having an amino acid sequence consisting of SEQ ID NO: 44, said heavy chain comprising three sequential CDRs having amino acid sequences consisting of SEQ ID NOS: 19, 20, and 21, and said light chain comprising three sequential CDRs having amino acid sequences consisting of SEQ ID NOS: 22, 23, and 24.

The 38SB31 antibody comprises at least one heavy chain having an amino acid sequence consisting of SEQ ID NO: 58 and at least one light chain having an amino acid sequence consisting of SEQ ID NO: 46, said heavy chain comprising three sequential CDRs having amino acid sequences consisting of SEQ ID NOS: 25, 26, and 27, and said light chain comprising three sequential CDRs having amino acid sequences consisting of SEQ ID NOS: 28, 29, and 30.

The 38SB39 antibody comprises at least one heavy chain having an amino acid sequence consisting of SEQ ID NO: 60 and at least one light chain having an amino acid sequence consisting of SEQ ID NO: 48, said heavy chain comprising three sequential CDRs having amino acid sequences consisting of SEQ ID NOS: 31, 32, and 33, and said light chain comprising three sequential CDRs having amino acid sequences consisting of SEQ ID NOS: 34, 35, and 36.

The hybridoma cell lines producing the 38SB13, 38SB18, 38SB19, 38SB30, 38SB31, and 38SB39 murine anti-CD38 antibodies have been deposited at the American Type Culture Collection (10801 University Bld, Manassas, Va., 20110-2209, USA), on Jun. 21, 2006, under the deposit numbers PTA-7667, PTA-7669, PTA-7670, PTA-7666, PTA-7668, and PTA-7671, respectively (as described in WO2008/047242 herein incorporated by reference in its entirety).

The term "humanized antibody", as used herein, refers to a chimeric antibody which contain minimal sequence derived from non-human immunoglobulin. The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modelling, statistical analysis and mutagenesis to alter the non-CDR surfaces of antibody variable regions to resemble the surfaces of known antibodies of the target host. The CDR grafting technology involves substituting the complementarity determining regions of, for example, a mouse antibody, into a human framework domain, e.g., see WO 92/22653 herein incorporated by reference in its entirety. Humanized chimeric antibodies may have constant regions and variable regions other than the complementarity determining regions (CDRs) derived substantially or exclusively from the corresponding human antibody regions and CDRs derived substantially or exclusively from a mammal other than a human.

Strategies and methods for the resurfacing of antibodies, and other methods for reducing immunogenicity of antibodies within a different host, are disclosed in U.S. Pat. No. 5,639,641, which is hereby incorporated in its entirety by reference. Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, *Molecular Immunology* 28(4/5): 489-498; Studnicka G. M. et al., 1994, *Protein Engineering*, 7(6): 805-814; Roguska M. A. et al., 1994, *PNAS*, 91: 969-973 herein incorporated by reference in its entirety), chain shuffling (U.S. Pat. No. 5,565,332 herein incorporated by reference in its entirety), and identification of flexible residues (PCT/US2008/074381 herein incorporated by reference in its entirety). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

The anti-CD38 antibodies of the pharmaceutical combination of the present invention are humanized antibodies which recognize CD38 and kill CD38$^+$ cells by apoptosis, ADCC, and CDC. In a further embodiment, the humanized antibodies of the invention are capable of killing said CD38$^+$ cells by apoptosis even in the absence of stroma cells or stroma-derived cytokines.

An embodiment of such a humanized antibody is a humanized 38SB13, 38SB18, 38SB19, 38SB30, 38SB31, or 38SB39 antibody, or an epitope-binding fragment thereof.

The CDRs of the 38SB13, 38SB18, 38SB19, 38SB30, 38SB31, and 38SB39 antibodies are identified by modeling and their molecular structures have been predicted. Thus, in one embodiment, this invention provides humanized antibodies or epitope-binding fragment thereof comprising one or more CDRs having an amino acid sequence selected from the group consisting of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 and 81. In an embodiment, a humanized version of 38SB13 is provided, which comprises at least one heavy chain and at least one light chain, wherein said heavy chain comprises three sequential complementarity-determining regions having amino acid sequences represented by SEQ ID NOS: 1, 2, and 3, and wherein said light chain comprises three sequential complementarity-determining regions having amino acid sequences represented by SEQ ID NOS: 4, 5, and 6. In another embodiment, a humanized version of 38SB18 is provided, which comprises at least one heavy chain and at least one light chain, wherein said heavy chain comprises three sequential complementarity-determining regions having amino acid sequences represented by SEQ ID NOS: 7, 8, and 9, and wherein said light chain comprises three sequential complementarity-determining regions having amino acid sequences represented by SEQ ID NOS: 10, 11, and 12. In another embodiment, a humanized version of 38SB19 is provided, which comprises at least one heavy chain and at least one light chain, wherein said heavy chain comprises three sequential complementarity-determining regions having amino acid sequences represented by SEQ ID NOS: 13, 14 (or 81), and 15, and wherein said light chain comprises three sequential complementarity-determining regions having amino acid sequences represented by SEQ ID NOS: 16, 17, and 18. In another embodiment, a humanized version of 38SB30 is provided, which comprises at least one heavy chain and at least one light chain, wherein said heavy chain comprises three sequential complementarity-determining regions having amino acid sequences represented by SEQ ID NOS: 19, 20, and 21, and wherein said light chain comprises three sequential complementarity-determining regions having amino acid sequences represented by SEQ ID NOS: 22, 23, and 24. In another embodiment, a humanized version of 38SB31 is provided, which comprises at least one heavy chain and at least one light chain, wherein said heavy chain comprises three sequential complementarity-determining regions having amino acid sequences represented by SEQ ID NOS: 25, 26, and 27, and wherein said light chain comprises three sequential complementarity-determining regions having amino acid sequences represented by SEQ ID NOS: 28, 29, and 30. In another embodiment, a humanized version of 38SB39 is provided, which comprises at least one heavy chain and at least one light chain, wherein said heavy chain comprises three sequential complementarity-determining regions having amino acid sequences represented by SEQ ID NOS: 31, 32, and 33, and wherein said light chain comprises three sequential complementarity-determining regions having amino acid sequences represented by SEQ ID NOS: 34, 35, and 36.

In one embodiment, this invention provides humanized antibodies or fragments thereof which comprise a $V_H$ having an amino acid sequence selected from the group of SEQ ID NOS: 66 and 72. In an embodiment, a humanized 38SB19 antibody is provided which comprises a $V_H$ having an amino acid sequence represented by SEQ ID NO: 66. In another embodiment, a humanized 38SB31 antibody is provided which comprises a $V_H$ having an amino acid sequence represented by SEQ ID NO: 72.

In another embodiment, this invention provides humanized antibodies or fragments thereof which comprise a $V_L$ having an amino acid sequence selected from the group of SEQ ID NOS: 62, 64, 68, and 70. In an embodiment, a humanized 38SB19 antibody is provided which comprises a $V_L$ having an amino acid sequence chosen from the group of SEQ ID NOS: 62 and 64. In another embodiment, a humanized 38SB31 antibody is provided which comprises a $V_L$ having an amino acid sequence chosen from the group of SEQ ID NOS: 68 and 70.

Each of the humanized versions of the 38SB13, 38SB18, 38SB19, 38SB30, 38SB31, and 38SB39 antibodies has been shown to be particularly advantageous as an anticancer agent. The preparation, physical properties and beneficial pharmacological properties thereof are described in WO 2008/047242, which is incorporated by reference herein in its entirety. Generally, the doses used for treating human beings, which depend on factors distinctive to the subject to be treated, are between 1 and 150 mg/kg, 10 and 100 mg/kg or 50 and 100 mg/kg administered orally or between 1 and 150 mg/kg, 10 and 100 mg/kg or 50 and 100 mg/kg administered intravenously.

Bortezomib is a boronic acid dipeptide ([(1R)-3-methyl-1-({(2S)-3-phenyl-2-[(pyrazin-2-ylcarbonyl)amino] propanoyl}amino)butyl]boronic acid; brand name: Velcade™) with antitumoral activity (Richardson et al., *N. Engl. J. Med.*, 352: 2487-2498, 2005). Bortezomib is a highly specific, reversible inhibitor of the 26 S proteasome. In normal cells, the proteasome regulates protein expression and function by degradation of ubiquitinylated proteins; in addition, it is involved in the elimination of misfolded proteins. The mechanism of action of bortezomib involves stabilization of NF-κB, p21, p27, p53, Bid, and Bax, inhibition of caveolin-1 activation, and activation of JNK as well as the endoplasmic reticulum stress response (Boccadoro et al. *Cancer Cell Int.*, 5(1): 18, 2005). While multiple mechanisms are likely to be involved, proteasome inhibition may thus permit activation of programmed cell death in neoplastic cells dependent upon suppression of pro-apoptotic pathways. Specifically, the agent inhibits nuclear factor (NF)-kappaB, thereby interfering with NF-kappaB-mediated cell survival, tumor growth, and angiogenesis. Bortezomib is thus used for treating multiple myeloma and mantle cell lymphoma. Bortezomib is usually administered intravenously.

It has now been found, and for this invention, that the efficacy of the humanized anti-CD38 antibodies may be considerably improved when it is administered in combination with at least one substance which is therapeutically useful in anticancer treatments and has a mechanism identical to or different from the one of the humanized anti-CD38 antibodies and which is limited in the present invention to bortezomib.

Moreover, since the activity of the products depends on the doses used, it is possible to use lower doses and to increase the activity while decreasing the toxicity phenomena. The improved efficacy of a combination according to the invention may be demonstrated by determination of the therapeutic synergy. A combination manifests therapeutic synergy if it is therapeutically superior to the best agent of the study used alone at its maximum tolerated dose or at its highest dose tested when toxicity cannot be reached in the animal species.

This efficacy may be quantified, for example, by the $\log_{10}$ cell kill, which is determined according to the following formula:

$$\log_{10} \text{ cell kill} = T - C(\text{days})/3.32 \times T_d$$

in which T–C represents the tumor growth delay, which is the median time in days for the tumors of the treated group (T) and the tumors of the control group (C) to have reached a predetermined value (1 g for example), and $T_d$ represents the time in days needed for the volume of the tumor to double in the control animals [T. H. Corbett et al., *Cancer*, 40: 2660-2680 (1977); F. M. Schabel et al., *Cancer Drug Development*, Part B, Methods in Cancer Research, 17: 3-51, New York, Academic Press Inc. (1979)]. A product is considered to be active if $\log_{10}$ cell kill is greater than or equal to 0.7. A product is considered to be very active if $\log_{10}$ cell kill is greater than or equal to 2.8.

The combination will manifest therapeutic synergy when the $\log_{10}$ cell kill is greater than the value of the $\log_{10}$ cell kill of the best constituent administered alone at its maximum tolerated dose or at its highest dose tested.

The efficacy of the combinations on solid tumors may be determined experimentally in the following manner:

The animals subjected to the experiment, generally mice, are subcutaneously grafted unilaterally or bilaterally with tumor cells or fragment on day 0. The animals bearing tumors are randomized based on their tumor size before being subjected to the various treatments and controls. Chemotherapy begins when tumors have reached a predetermined size after grafting, depending on the type of tumor, and the animals are observed every day. The different animal groups are weighed daily during treatment until the maximum weight loss is reached and subsequent full weight recovery has occurred. The groups are then weighed once or twice a week until the end of the trial.

The tumors are measured 1 to 5 times a week, depending on the tumor doubling time, until the tumor reaches approximately 750 mg, or until the animal dies (if this occurs before the tumor reaches 750 mg). The animals are necropsied immediately after euthanasia or death.

The antitumor activity is determined in accordance with the different parameters recorded.

Results obtained with combinations of hu38SB19 and bortezomib used at their optimal doses are indicated hereunder as examples.

The present invention also relates, therefore, to pharmaceutical compositions containing the combinations according to the invention.

The constituents of which the combination are composed may be administered simultaneously, semi-simultaneously, separately, or spaced out over a period of time so as to obtain the maximum efficacy of the combination; it being possible for each administration to vary in its duration from a rapid administration to a continuous perfusion.

The timing between at least one administration of antibody specifically recognizing CD38, and at least one administration of bortezomib is approximately 1 month or less or approximately 2 weeks or less, or approximately 1 day or less.

As a result, for the purposes of the present invention, the combinations are not exclusively limited to those which are obtained by physical association of the constituents, but also to those which permit a separate administration, which can be simultaneous or spaced out over a period of time.

The compositions according to the invention are preferably compositions which can be administered parentally. However, these compositions may be administered orally, subcutaneously or intraperitoneally in the case of localized regional therapies.

The compositions for parental administration are generally pharmaceutically acceptable, sterile solutions or suspensions which may optionally be prepared as required at the time of use. For the preparation of non-aqueous solutions or suspensions, natural vegetable oils such as olive oil, sesame oil or liquid petroleum or injectable organic esters such as ethyl oleate may be used. The sterile aqueous solutions can consist of a solution of the product in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition. The combinations may also take the form of liposomes or the form of an association with carriers as cyclodextrins or polyethylene glycols.

The compositions for oral, subcutaneous or intraperitoneal administration may be preferably aqueous suspensions or solutions.

In the combinations according to the invention, the application of the constituents of which may be simultaneous, separate or spaced out over a period of time, it is especially advantageous for the amount of humanized anti-CD38 antibody to represent from 10 to 90% by weight of the combination, it being possible for this content to vary in accordance with the nature of the associated substance, the efficacy sought and the nature of the cancer to be treated.

The combinations according to the invention are especially useful in the treatment of several types of cancers including (but not limited to) the following: carcinoma and adenocarcinoma, including that of the bladder, breast, colon, head-and-neck, prostate, kidney, liver, lung, ovary, pancreas, stomach, cervix, thyroid and skin, and including squamous cell carcinoma; hematopoietic tumors of lymphoid lineage, including multiple myeloma, leukemia, acute and chronic lymphocytic (or lymphoid) leukemia, acute and chronic lymphoblastic leukemia, B-cell lymphoma, T-cell lymphoma, non-Hodgkin lymphoma (e.g., Burkitt's); hematopoietic tumors of myeloid lineage, including acute and chronic myelogenous (myeloid or myelocytic) leukemias, and promyelocytic leukemia; tumors of mesenchymal origin, including fibrosarcoma, osteosarcoma and rhabdomyosarcoma; tumors of the central and peripheral nervous system, including astrocytoma, neuroblastoma, glioma, and schwannomas; and other tumors, including melanoma, teratocarcinoma, xeroderma pigmentosum, keratoacanthoma, and seminoma, and other cancers yet to be determined in which CD38 is expressed. They are mainly useful for treating leukemia, lymphoma and cancers resistant to the commonly used anticancer agents as the anti-CD38 antibodies of the invention have a unique mechanism of action.

In an embodiment the antitumor efficacy of the combination is about 11-42% T/C. T/C (%) is the ratio Median tumor volume of the treated/Median tumor volume of the control× 100.

In another embodiment the antitumor efficacy of the combination is about 0-10% T/C.

Thus, an aspect of the invention is the above combinations for use in the treatment of cancer. In another aspect, the invention also encompasses the use of the above combinations for the manufacture of a medicament for the treatment of cancer.

Another embodiment of the invention is an article of manufacture comprising:
a) a packaging material
b) a combination of an antibody specifically recognizing CD38 and at least bortezomib, wherein said antibody is capable of killing a $CD38^+$ cell by apoptosis, antibody-dependent cell-mediated cytotoxicity (ADCC), and complement-dependent cytoxicity (CDC), and
c) a label or package insert contained within said packaging material indicting that said combination thereof is effective for treating cancer.

EXAMPLE

In this example, the effectiveness of an anti-CD38 antibody/bortezomib combination of the invention for tumor growth inhibition was demonstrated in vivo.

Test Article Administration:

Hu38SB19 and Bortezomib treatments were started thirty four days after cell inoculation and doses were calculated based on individual animal body weights determined from the last measurement taken before dosing. Administration of PBS and hu38SB19 antibody was carried out through intraperitoneal (IP) injection and bortezomib by intravenous (IV) injection via the tail vein, using a 1.0 mL syringe fitted with a 27 gauge, ½ inch needle.

Specific Study Design:

The NCI-H929 multiple myeloma subcutaneous xenograft model was initiated in female CB.17 SCID mice by subcutaneous injection of $1 \times 10^7$ cells per mouse, suspended in 0.1 ml serum-free culture medium.

Thirty-three days after tumor cell inoculation, sixty-four mice were randomized into 8 groups (n=8) by tumor volume. The tumor volumes ranged from 86.7 to 355.2 (189.0±74.3, Median±SD) $mm^3$. Body weights of the mice ranged from 17.2 to 22.4 (19.4±1.1, Median±SD) grams. Mice in each group were identified by a puncture in the ear.

Treatment groups included PBS control (200 μL/mouse/treatment), hu38SB19 antibody (5.0 mg/kg/treatment), bortezomib (1.0, 0.6 and 0.4 mg/kg/treatment) and three combination groups with hu38SB19 (5.0 mg/kg/treatment) and bortezomib (1.0, 0.6 and 0.4 mg/kg/treatment). PBS, hu38SB19 and bortezomib were administered twice per week for one week (days 34 and 37 for a total of 2 treatments). Treatments were started on day 34 post inoculation of tumor cells.

Tumor volumes were measured one to two times weekly in three dimensions using a caliper. The tumor volume was expressed in $mm^3$ (or mg) using the formula: V=Length× Width×Height×½.

Body weights were measured twice per week as a rough index of test agent toxicity. Tumor volume and body weight were determined and recorded by Labcat software.

Results:

The anti-tumor activity of the hu38SB19 antibody and bortezomib alone and in combination was evaluated in female SCID mice bearing subcutaneous NCI-H929 tumor xenografts, a human multiple myeloma model.

The following end points were used:

Toxicity was declared at dosages inducing 20% body weight loss or 10% drug death, Antitumor efficacy was determined by calculating:

$$T/C(\%)=\text{Median tumor volume of the treated/Median tumor volume of the control} \times 100,$$

wherein a T/C≤42% is the minimum level of anti-tumor activity. A T/C<10% is considered a high anti-tumor activity level;

$\log_{10}$ cell kill=(T−C value in days)/(3.32×Td in days)]

wherein T, C, and Td are as defined above. No antitumor activity was declared for log cell kill<0.7.

Tumor Free Survivors (TFS): correspond to complete regression below the limit of palpation (63 mg) for the entire duration of the study (>100 days post last treatment).

Therapeutic Synergism: a combination has therapeutic synergism if it is more active than the best single agent of the study.

Hu38SB19 antibody alone at 5.0 mg/kg/injection had marginal anti-tumor activity with a % T/C of 41% and a $\log_{10}$ cell kill of 0.5 (see Table 1).

Likewise, bortezomib alone was inactive for doses of 0.4 and 0.6 mg/kg/injection, with T/C of 45 and 75%, and $\log_{10}$ cell kill of 0.1 and 0.3, respectively. No TFS was observed at 0.6 mg/kg/injection, whereas a single TFS was obtained with 0.4 mg/kg/injection. Only, the highest dosed tested of bortezomib (1.0 mg/kg/injection) was somewhat active with a % T/C of 15% and 2 TFS obtained; however, the $\log_{10}$ cell kill was only of 0.6.

On the other hand, the combination of hu38SB19 antibody (5.0 mg/kg/injection) and bortezomib is active even at the lowest doses. Indeed, when huSB3819 is administered with 0.4 and 0.6 mg/kg/injection, the % T/C is 8.7 and 11%, respectively. In both cases, the $\log_{10}$ cell kill was around 1 (0.9 and 1.5.respectively), and 3 TFS, out of 8 mice, obtained with the combinations.

Thus, the combination of hu38SB19 antibody (5 mg/kg/injection) and bortezomib (0.4, 0.6 and 1.0 mg/kg/injection) demonstrated greater activity than the best single agent of the study (bortezomib).

We conclude that the combination of the hu38SB19 antibody and bortezomib show therapeutic synergism.

TABLE I

Combination of hu38SB19 and bortezomib against multiple myeloma NCI-H929 implanted in SCID mice.

| Agent, route | Dosage in mg/kg/ Injection (total dose) | Schedule in days | Average body weight loss in % per mouse at nadir (day of nadir) | Time for median tumor to reach 750 mg in days | % T/C | T-C in days | log cell kill | TFS at day 176 | Comments |
|---|---|---|---|---|---|---|---|---|---|
| PBS | | | * | 62 | | | | | |
| Hu38SB19, IP | 5 (10) | 34, 37 | * | 92 | 41 | 30 | 0.5 | 2/8 | Marginaly Active |
| | 1.0 (2.0) | 34, 37 | 7.0 (d36) | 99 | 15 | 37 | 0.6 | 2/8 | Active |
| Bortezomib, IV | 0.6 (1.2) | 34, 37 | 0.6 (d40) | 80 | 45 | 18 | 0.3 | 0/8 | Inactive |
| | 0.4 (0.8) | 34, 37 | 0.8 (d36) | 69 | 74 | 7 | 0.1 | 1/8 | Inactive |
| Hu38SB19, IP & bortezomib, IV | 5 (10) & 1.0 (2.0) | 34, 37 | 7.5 (d36) | 142 | 0 | 80 | 1.2 | 6/8 | Highly Active |
| | 5 (10) & 0.6 (1.2) | 34, 37 | 2.0 (d40) | 156 | 11 | 94 | 1.5 | 3/8 | Active |
| | 5 (10) & 0.4 (0.8) | 34, 37 | 4.7 (d40) | 122 | 8.7 | 60 | 0.9 | 3/8 | Highly Active |

NCI-H929 tumor cells implanted sc. $1.0 \times 10^7$ cells/mouse. Tumor doubling time = 19.5 days. Median tumor size at start of therapy =153-201 mg., T-C = tumor growth delay, TFS = tumor free survivors,. Formulations: hu38SB19 = phosphate buffer saline without $Ca^{2+}$ and $Mg^{2+}$, pH 7.4, bortezomib = glucose 5% in water.

The invention claimed is:

1. A pharmaceutical combination comprising an antibody specifically recognizing CD38 and at least bortezomib, wherein said antibody comprises at least one heavy chain and at least one light chain, wherein said heavy chain comprises three sequential complementarity determining regions comprising the amino acid sequences of SEQ ID NOs: 13, 14 (or 81) and 15, and wherein said light chain comprises three sequential complementarity determining regions comprising the amino acid sequences of SEQ ID NOs: 16, 17 and 18, and wherein the antibody and bortezomib constituents of the combination are physically separate.

2. The combination of claim 1, wherein said antibody is a chimeric or a humanized antibody.

3. The combination of claim 1 wherein said antibody comprises at least one heavy chain and at least one light chain, wherein said heavy chain comprises the amino acid sequence of SEQ ID NO: 66, and wherein said light chain comprises an amino acid sequence selected from the group consisting of SEQ ID NOS: 62 and 64.

4. A method for treating a CD38+-expressing cancer in a subject, the method comprising administering a pharmaceutical combination comprising an antibody specifically recognizing CD38 and at least bortezomib to the subject, said antibody comprises at least one heavy chain and at least one light chain, wherein said heavy chain comprises three sequential complementarity determining regions comprising the amino acid sequences of SEQ ID NOs: 13, 14 (or 81) and 15, and wherein said light chain comprises three sequential complementarity determining regions comprising the amino acid sequences of SEQ ID NOs: 16, 17 and 18, and wherein the antibody and bortezomib constituents of the combination are physically separate, thereby treating the cancer in the subject.

5. The method of claim 4, wherein said antibody is a chimeric or humanized antibody.

6. The method of claim 4, wherein said heavy chain comprises the amino acid sequence of SEQ ID NO: 66, and wherein said light chain comprises an amino acid sequence selected from the group consisting of SEQ ID NOS: 62 and 64.

7. The method of claim 4, wherein the constituents of said combination are administered simultaneously.

8. The method of claim 4, wherein the constituents of said combination are spaced out over a period of time.

9. An article of manufacture comprising:
a) a packaging material
b) a combination of an antibody specifically recognizing CD38 and at least bortezomib, wherein said antibody comprises at least one heavy chain and at least one light chain, wherein said heavy chain comprises three sequential complementarity determining regions comprising the amino acid sequences of SEQ ID NOs: 13, 14 (or 81) and 15, and wherein said light chain comprises three sequential complementarity determining regions comprising the amino acid sequences of SEQ ID NOs: 16, 17 and 18, and wherein the antibody and bortezomib constituents of the combination are physically separate, and
c) a label or package insert contained within said packaging material indicating that said combination thereof is effective for treating a CD38+-expressing cancer.

10. The method of claim 4, wherein said cancer is a hematopoietic tumor of myeloid or lymphoid lineage.

11. The combination of claim 1, wherein said antibody is capable of killing a $CD38^+$ cell by apoptosis, antibody-dependent cell-mediated cytotoxicity (ADCC), and complement-dependent cytotoxicity (CDC).

12. The method of claim 4, wherein said antibody is capable of killing a $CD38^+$ cell by apoptosis, antibody-dependent cell-mediated cytotoxicity (ADCC), and complement-dependent cytotoxicity (CDC).

13. The combination of claim 1, wherein said antibody comprises a light chain comprising an amino acid sequence of SEQ ID NO: 62 and a heavy chain comprising an amino acid sequence of SEQ ID NO: 66.

14. The method of claim 4, wherein said antibody comprises a light chain comprising an amino acid sequence of SEQ ID NO: 62 and a heavy chain comprising an amino acid sequence of SEQ ID NO: 66.

* * * * *